United States Patent [19]
Chinnadurai

[11] Patent Number: 5,773,599
[45] Date of Patent: Jun. 30, 1998

[54] 48 KD CELLULAR PHOSPHOPROTEIN CTBP

[75] Inventor: Govindaswamy Chinnadurai, St. Louis, Mo.

[73] Assignee: Saint Louis University, St. Louis, Mo.

[21] Appl. No.: 553,999

[22] Filed: Nov. 6, 1995

[51] Int. Cl.$^6$ .................... C07H 21/04; G01N 33/536; C07K 14/00
[52] U.S. Cl. .................... 536/23.1; 436/536; 530/350
[58] Field of Search ................ 435/172.1; 424/233.1; 536/23.1; 436/536; 530/350

[56] References Cited

PUBLICATIONS

Boyd et al. EMBO J vol. 12, No. 2, pp. 469–478, 1993.
PNAS USA vol. 92, No. 23, Nov. 7, 1995, pp. 10467–10471.

Primary Examiner—Ponnathapura Achutamurthy
Assistant Examiner—Phuong T. Bui

[57] ABSTRACT

Cloning of the cDNA for CtBP via yeast two hybrid interaction cloning. The DNA encodes a 439 amino acid (48 kD) protein that specifically interacts with exon 2. This protein requires residues 225–238 of the 243R E1A protein for interaction. The predicted protein sequence of the isolated cDNA is identical to amino acid sequences obtained from peptides prepared from biochemically purified CtBP. Fine mapping of the CtBP-binding domain revealed that a six amino acid motif highly conserved among the E1A proteins of various human and animal adenoviruses is required for this interaction.

2 Claims, 9 Drawing Sheets

ΔPL ΔDL ΔSC
Ad2 243R  222 ...ciedllnepgq[PLDLSC]krprp 243
              AS  AS  AS Ad12 235R  214 ...iqeeereqtvPVDLSVkrprcn 235

FIG. 6A

```
  1  MGSSHLLLNKG  LPLGVRPPIM  NGPLHPRPLV  ALLDGRDCTV  EMPILKDVAT
 51  VAFCDAQSTQ   EIHEKVLNEA  VGALMYHTIT  LTREDLEKFK  ALRIIVRIGS
101  GFDNIDIKSA   GDLGIAVCNV  PAASVEETAD  STLCHILNLY  RRATGCTRRC
        ───A───
151  GRAHESRASS   RSARWRPRCQ  DPRGDLGHHR  TWSRGAGSGA  AGQRVGFNVL
201  FYDPYLSDGV   ERALGLQRVS  TLQDLLFHSD  CVTLHCGLNE  HNHHLINDFT
251  VKQMRQGAFL   VNTARGGLVD  EKALAQALKE  GRIRGAALDV  HESEPFSFSQ
     ─────────B──────
301  GPLKDAPNLI   CTPHAAWYSE  AREIRRAITG  RIPDSLKNCV
351  NKDHLTAATH   WASMDPAVVH  PELNGAAYRY  PPGVVGVAPT  GIPAAVEGIV
401  PSAMSLSHGL   PPVAHPPHAP  SPGQTVKPEA  DRDHASDQL
```

FIG. 6B

```
vanH 188 FDELLQNSDIVTLHVPLNTDTHYIISHEQIQRMKQGAFLINTGRGPLVDTYELVKALENG 247
         :::|| :||.|||| .||...|..:|.  ..:|:|||||||.|||.  |..||..:|
CtBP 222 lqdllfhsdcvtlhcglnehnhhlindftvkqmrggaflvntargglvdekaïagalkeg 281 vanH 248 KLGGAALDVLEGEEEFFYSDCTQKPIDNQFLLKLQRMPNVIITPHTAYYTEQA 300
         ::  ||||||  |: |.| :|:..            |. ||:.:.|||.|||:|:|||
CtBP 282 rirgaaldvṼhes.epfsfsqgp..........lkdapnlictphaawyseqa 322
```

FIG. 7

GCGCAGGCCGCCGAGGGTCGGGGCCCGCGCCGGCTCGCGCCTCTCGATGGGCAGCTCGCA
CTTGCTCAACAAGGGCCTGCCGCTTGGCGTCCGACCTCCGATCATGAACGGGCCCCTGCA
CCCGCGGCCCCTGGTGGCATTGCTGGATGGCCGGGACTGCACAGTGGAGATGCCCATCCT
GAAGGACGTGGCCACTGTGGCCTTCTGCGACGCGCAGTCCACGCAGGAGATCCATGAGAA
GGTCCTGAACGAGGCTGTGGGGGCCCTGATGTACCACACCATCACTCTCACCAGGGAGGA
CCTGGAGAAGTTCAAAGCCCTCCGCATCATCGTCCGGATTGGCAGTGGTTTTGACAACAT
CGACATCAAGTCGGCCGGGGATTTAGGCATTGCCGTCTGCAACGTGCCCGCGGCGTCTGT
GGAGGAGACGGCCGACTCGACGCTGTGCCACATCCTGAACCTGTACCGGCGGGCCACTGG
CTGCACCAGGCGCTGCGGGAGGGCACACGAGTCCAGAGCGTCGAGCAGATCCGCGAGGTG
GCGTCCGCGCTGCCAGGATCCGCGGGGAGACCTTGGGCATCATCGGACTTGGTCGCGTGG
GGCAGGCAGTGGCGCTGCGGGCCAACGTGTCGGCTTCAACGTGCTCTTCTACGACCCTTA
CTTGTCGGATGGCGTGGAGCGGGCGCTGGGCTGCAGCGTGTCAGCACCCTGCAGGACCT
GCTCTTCCACAGCGACTGCGTGACCCTGCACTGCGGCCTCAACGAGCACAACCACCACCT
CATCAACGACTTCACCGTCAAGCAGATGAGACAAGGGGCCTTCCTGGTGAACACAGCCCG
GGGTGGCCTGGTGGATGAGAAGGCGCTGGCCCAGGCCCTGAAGGAGGGCCGGATCCGCGG
CGCGGCCCTGGATGTGCACGAGTCGGAACCCTTCAGCTTTAGCCAGGGCCCTCTGAAGGA
TGCACCCAACCTCATCTGCACCCCCATGCTGCATGGTACAGCGAGCAGGCATCCATCGA
GATGCGAGAGGAGGCGGCACGGGAGATCCGCAGAGCCATCACAGGCCGGATCCCAGACAG
CCTGAAGAACTGTGTCAACAAGGACCATCTGACAGCCGCCACCCACTGGGCCAGCATGGA
CCCCGCCGTCGTGCACCCTGAGCTCAATGGGGCTGCCTATAGGTACCCTCCGGGCGTGGT
GGGCGTGGCCCCCACTGGCATCCCAGCTGCTGTGGAAGGTATCGTCCCCAGCGCCATGTC
CCTGTCCCACGGCCTGCCCCTGTGGCCCACCCGCCCCACGCCCCTTCTCCTGGCCAAAC
CGTCAAGCCCGAGGCGGATAGAGACCACGCCAGTGACCAGTTGTAGCCCGGGAGGAGCTC
TCCAGCCTCGGCGCCTGGGGCAGCGGGCCCGGAAACCCTCGACCAGAGTGTGTGAGAGCA
TGTGTGTGGTGGCCCCTGGCACTGCAGAGACTGGTCCGGGCTGTCAGGAGGGCGGGAGGG
CGCAGCGCTGGGCCTCGTGTCGCTTGTCGTCCGTCCTGTGGGCGCTCTGCCCTGTGTCCT
TCGCGTTCCTCGTTAAGCAGAAGAAGTCAGTAGTTATTCTCCCATGAACGTTCTTGTCTG
TGTACAGTTTTTAGAACATTACAAAGGATCTGTTTGCTTAGCTGTCAACAAAAGAAAAC
CTGAAGGAGCATTTGGAAGTCAATTTGAGGTTTTTTTTTTGGTTTTTTTTTTTTGTAT
TTTGGAACGTGCCCCAGAATGAGGCAGTTGGCAAACTTCTCAGGACAATGAATCTTCCCG
TTTTTCTTTTTATGCCACACAGTGCATTGTTTTTCTACCTGCTTGTCTTATTTTTAGCA
TAATTTAGAAAAACAAAACAAAGGCTGTTTTCCTAATTTTGGCATGAACCCCCCCTTGT
TCCAAAATGAAGACGGCATCATCACGAAGCAGCTCCAAAAGGAAAAGCTTGGCAGGTGCC
CTCGTCCTGGGGACGTGGAGGGTGGCACGGTCCCCGCCTGCACCAGTGCCGTCCTGCTGA
TGTGGTAGGCTAGCAATATTTTGGTTAAAATCATGTTTGTGGCCGAACGGGCCCCTGCAC
CCG

SEQUENCE LISTING ( 1 ) GENERAL INFORMATION:

( i i i ) NUMBER OF SEQUENCES:2

( 2 ) INFORMATION FOR SEQ ID NO: 1:

( i ) SEQUENCE CHARACTERISTICS:
        ( A ) LENGTH:2085 base pairs
        ( B ) TYPE:nucleic acid
        ( C ) STRANDEDNESS:single
        ( D ) TOPOLOGY:linear     ( i i ) MOLECULE TYPE:cDNA     ( i i i ) HYPOTHETICAL:no     ( i v ) ANTI-SENSE:no     ( v i ) ORIGINAL SOURCE:
        ( A ) ORGANISM:human
        ( C ) INDIVIDUAL ISOLATE: pACT30
        ( G ) CELL TYPE:B-cell     ( v i i ) IMMEDIATE SOURCE:
        ( A ) LIBRARY:cDNA
        ( B ) CLONE:pACT30

( x ) PUBLICATION INFORMATION:
        ( A ) AUTHORS:Ute Schaeper
            Janice M. Boyd
            Sulekha Verma
            Erik Uhlmann
            T. Subramanian
            G. Chinnadurai
        ( B ) TITLE: Molecular cloning and characterization of a
            cellular phosphoprotein that interacts with a conserved
            carboxy- negative modulation of oncogenic transformation.
        ( C ) JOURNAL:Proceedings of the National Academy of Sciences
            United States of America
        ( D ) VOLUME:92
        ( C ) ISSUE:23
        ( D ) PAGES:10667-10671
        ( K ) RELEVANT RESIDUES IN SEQ ID NO: 1:

( i x ) SEQUENCE DESCRIPTION:SEQ ID NO: 1:

```
GCGCAGGCCG  CCGAGGGTCG  GGGCCCGCGC  CGGCTCGCGC  CTCTCGATGG  GCAGCTCGCA      60

CTTGCTCAAC  AAGGGCCTGC  CGCTTGGCGT  CCGACCTCCG  ATCATGAACG  GGCCCCTGCA     120

CCCGCGGCCC  CTGGTGGCAT  TGCTGGATGG  CCGGGACTGC  ACAGTGGAGA  TGCCCATCCT     180

GAAGGACGTG  GCCACTGTGG  CCTTCTGCGA  CGCGCAGTCC  ACGCAGGAGA  TCCATGAGAA     240

GGTCCTGAAC  GAGGCTGTGG  GGGCCCTGAT  GTACCACACC  ATCACTCTCA  CCAGGGAGGA     300

CCTGGAGAAG  TTCAAAGCCC  TCCGCATCAT  CGTCCGGATT  GGCAGTGGTT  TTGACAACAT     360

CGACATCAAG  TCGGCCGGGG  ATTTAGGCAT  TGCCGTCTGC  AACGTGCCCG  CGGCGTCTGT     420

GGAGGAGACG  GCCGACTCGA  CGCTGTGCCA  CATCCTGAAC  CTGTACCGGC  GGGCCACTGG     480

CTGCACCAGG  CGCTGCGGGA  GGGCACACGA  GTCCAGAGCG  TCGAGCAGAT  CCGCGAGGTG     540

GCGTCCGCGC  TGCCAGGATC  CGCGGGGAGA  CCTTGGGCAT  CATCGGACTT  GGTCGCGTGG     600

GGCAGGCAGT  GGCGCTGCGG  GCCAACGTGT  CGGCTTCAAC  GTGCTCTTCT  ACGACCCTTA     660

CTTGTCGGAT  GGCGTGGAGC  GGGCGCTGGG  GCTGCAGCGT  GTCAGCACCC  TGCAGGACCT     720
```

| | | | | | |
|---|---|---|---|---|---|
| GCTCTTCCAC | AGCGACTGCG | TGACCCTGCA | CTGCGGCCTC | AACGAGCACA | ACCACCACCT | 780 |
| CATCAACGAC | TTCACCGTCA | AGCAGATGAG | ACAAGGGGCC | TTCCTGGTGA | ACACAGCCCG | 840 |
| GGGTGGCCTG | GTGGATGAGA | AGGCGCTGGC | CCAGGCCCTG | AAGGAGGGCC | GGATCCGCGG | 900 |
| CGCGGCCCTG | GATGTGCACG | AGTCGGAACC | CTTCAGCTTT | AGCCAGGGCC | CTCTGAAGGA | 960 |
| TGCACCCAAC | CTCATCTGCA | CCCCCCATGC | TGCATGGTAC | AGCGAGCAGG | CATCCATCGA | 1020 |
| GATGCGAGAG | GAGGCGGCAC | GGGAGATCCG | CAGAGCCATC | ACAGGCCGGA | TCCCAGACAG | 1080 |
| CCTGAAGAAC | TGTGTCAACA | AGGACCATCT | GACAGCCGCC | ACCCACTGGG | CCAGCATGGA | 1140 |
| CCCCGCCGTC | GTGCACCCTG | AGCTCAATGG | GGCTGCCTAT | AGGTACCCTC | CGGGCGTGGT | 1200 |
| GGGCGTGGCC | CCCACTGGCA | TCCCAGCTGC | TGTGGAAGGT | ATCGTCCCCA | GCGCCATGTC | 1260 |
| CCTGTCCCAC | GGCCTGCCCC | CTGTGGCCCA | CCCGCCCCAC | GCCCCTTCTC | CTGGCCAAAC | 1320 |
| CGTCAAGCCC | GAGGCGGATA | GAGACCACGC | CAGTGACCAG | TTGTAGCCCG | GGAGGAGCTC | 1380 |
| TCCAGCCTCG | GCGCCTGGGG | CAGCGGGCCC | GGAAACCCTC | GACCAGAGTG | TGTGAGAGCA | 1440 |
| TGTGTGTGGT | GGCCCCTGGC | ACTGCAGAGA | CTGGTCCGGG | CTGTCAGGAG | GGCGGGAGGG | 1500 |
| CGCAGCGCTG | GGCCTCGTGT | CGCTTGTCGT | CCGTCCTGTG | GGCGCTCTGC | CCTGTGTCCT | 1560 |
| TCGCGTTCCT | CGTTAAGCAG | AAGAAGTCAG | TAGTTATTCT | CCCATGAACG | TTCTTGTCTG | 1620 |
| TGTACAGTTT | TTAGAACATT | ACAAAGGATC | TGTTTGCTTA | GCTGTCAACA | AAAAGAAAAC | 1680 |
| CTGAAGGAGC | ATTTGGAAGT | CAATTTGAGG | TTTTTTTTTT | TGGTTTTTTT | TTTTTGTAT | 1740 |
| TTTGGAACGT | GCCCCAGAAT | GAGGCAGTTG | GCAAACTTCT | CAGGACAATG | AATCTTCCCG | 1800 |
| TTTTTCTTTT | TATGCCACAC | AGTGCATTGT | TTTTCTACC | TGCTTGTCTT | ATTTTTAGCA | 1860 |
| TAATTTAGAA | AAACAAAACA | AAGGCTGTTT | TTCCTAATTT | TGGCATGAAC | CCCCCCTTGT | 1920 |
| TCCAAAATGA | AGACGGCATC | ATCACGAAGC | AGCTCCAAAA | GGAAAAGCTT | GGCAGGTGCN | 1980 |
| CCTCGTCCTG | GGGACGTGGA | GGGTGGCACG | GTCCCGCCT | GCACCAGTGC | CGTCCTGCTG | 2040 |
| ATGTGGTAGG | CTAGCAATAT | TTTGGTTAAA | ATCATGTTTG | TGGCC | | 2085 |

( 2 ) INFORMATION FOR SEQ ID NO: 2:

( i ) SEQUENCE CHARACTERISTICS:
        ( A ) LENGTH:439 amino acids
        ( B ) TYPE:amino acid
        ( C ) STRANDEDNESS:single
        ( D ) TOPOLOGY:linear     ( i i ) MOLECULE TYPE:protein     ( i i i ) HYPOTHETICAL:yes     ( i x ) SEQUENCE DESCRIPTION:SEQ ID NO: 2:

| Met | Gly | Ser | Ser | His | Leu | Leu | Asn | Lys | Gly | Leu | Pro | Leu | Gly | Val |
|---|---|---|---|---|---|---|---|---|---|---|---|---|---|---|
| | | | | 5 | | | | | 10 | | | | | 15 |
| Arg | Pro | Pro | Ile | Met | Asn | Gly | Pro | Leu | His | Pro | Arg | Pro | Leu | Val |
| | | | | 20 | | | | | 25 | | | | | 30 |
| Ala | Leu | Leu | Asp | Gly | Arg | Asp | Cys | Thr | Val | Glu | Met | Pro | Ile | Leu |
| | | | | 35 | | | | | 40 | | | | | 45 |
| Lys | Asp | Val | Ala | Thr | Val | Ala | Phe | Cys | Asp | Ala | Gln | Ser | Thr | Gln |
| | | | | 50 | | | | | 55 | | | | | 60 |
| Glu | Ile | His | Glu | Lys | Val | Leu | Asn | Glu | Ala | Val | Gly | Ala | Leu | Met |
| | | | | 65 | | | | | 70 | | | | | 75 |
| Tyr | His | Thr | Ile | Thr | Leu | Thr | Arg | Glu | Asp | Leu | Glu | Lys | Phe | Lys |
| | | | | 80 | | | | | 85 | | | | | 90 |
| Ala | Leu | Arg | Ile | Ile | Val | Arg | Ile | Gly | Ser | Gly | Phe | Asp | Asn | Ile |

|   |   |   |   |   | 95 |   |   |   | 100 |   |   |   | 105 |
|---|---|---|---|---|---|---|---|---|---|---|---|---|---|
| Asp | Ile | Lys | Ser | Ala | Gly | Asp | Leu | Gly | Ile | Ala | Val | Cys | Asn | Val |
|   |   |   |   | 110 |   |   |   | 115 |   |   |   | 120 |
| Pro | Ala | Ala | Ser | Val | Glu | Glu | Thr | Ala | Asp | Ser | Thr | Leu | Cys | His |
|   |   |   |   | 125 |   |   |   | 130 |   |   |   | 135 |
| Ile | Leu | Asn | Leu | Tyr | Arg | Arg | Ala | Thr | Gly | Cys | Thr | Arg | Arg | Cys |
|   |   |   |   | 140 |   |   |   | 145 |   |   |   | 150 |
| Gly | Arg | Ala | His | Glu | Ser | Arg | Ala | Ser | Ser | Arg | Ser | Ala | Arg | Trp |
|   |   |   |   | 155 |   |   |   | 160 |   |   |   | 165 |
| Arg | Pro | Arg | Cys | Gln | Asp | Pro | Arg | Gly | Asp | Leu | Gly | His | His | Arg |
|   |   |   |   | 170 |   |   |   | 175 |   |   |   | 180 |
| Thr | Trp | Ser | Arg | Gly | Ala | Gly | Ser | Gly | Ala | Ala | Gly | Gln | Arg | Val |
|   |   |   |   | 185 |   |   |   | 190 |   |   |   | 195 |
| Gly | Phe | Asn | Val | Leu | Phe | Tyr | Asp | Pro | Tyr | Leu | Ser | Asp | Gly | Val |
|   |   |   |   | 200 |   |   |   | 205 |   |   |   | 210 |
| Glu | Arg | Ala | Leu | Gly | Leu | Gln | Arg | Val | Ser | Thr | Leu | Gln | Asp | Leu |
|   |   |   |   | 215 |   |   |   | 220 |   |   |   | 225 |
| Leu | Phe | His | Ser | Asp | Cys | Val | Thr | Leu | His | Cys | Gly | Leu | Asn | Glu |
|   |   |   |   | 230 |   |   |   | 235 |   |   |   | 240 |
| His | Asn | His | His | Leu | Ile | Asn | Asp | Phe | Thr | Val | Lys | Gln | Met | Arg |
|   |   |   |   | 245 |   |   |   | 250 |   |   |   | 255 |
| Gln | Gly | Ala | Phe | Leu | Val | Asn | Thr | Ala | Arg | Gly | Gly | Leu | Val | Asp |
|   |   |   |   | 260 |   |   |   | 265 |   |   |   | 270 |
| Glu | Lys | Ala | Leu | Ala | Gln | Ala | Leu | Lys | Glu | Gly | Arg | Ile | Arg | Gly |
|   |   |   |   | 275 |   |   |   | 280 |   |   |   | 285 |
| Ala | Ala | Leu | Asp | Val | His | Glu | Ser | Glu | Pro | Phe | Ser | Phe | Ser | Gln |
|   |   |   |   | 290 |   |   |   | 295 |   |   |   | 300 |
| Gly | Pro | Leu | Lys | Asp | Ala | Pro | Asn | Leu | Ile | Cys | Thr | Pro | His | Ala |
|   |   |   |   | 305 |   |   |   | 310 |   |   |   | 315 |
| Ala | Trp | Tyr | Ser | Glu | Gln | Ala | Ser | Ile | Glu | Met | Arg | Glu | Glu | Ala |
|   |   |   |   | 320 |   |   |   | 325 |   |   |   | 330 |
| Ala | Arg | Glu | Ile | Arg | Arg | Ala | Ile | Thr | Gly | Arg | Ile | Pro | Asp | Ser |
|   |   |   |   | 335 |   |   |   | 340 |   |   |   | 345 |
| Leu | Lys | Asn | Cys | Val | Asn | Lys | Asp | His | Leu | Thr | Ala | Ala | Thr | His |
|   |   |   |   | 350 |   |   |   | 355 |   |   |   | 360 |
| Trp | Ala | Ser | Met | Asp | Pro | Ala | Val | Val | His | Pro | Glu | Leu | Asn | Gly |
|   |   |   |   | 365 |   |   |   | 370 |   |   |   | 375 |
| Ala | Ala | Tyr | Arg | Tyr | Pro | Pro | Gly | Val | Val | Gly | Val | Ala | Pro | Thr |
|   |   |   |   | 380 |   |   |   | 385 |   |   |   | 390 |
| Gly | Ile | Pro | Ala | Ala | Val | Glu | Gly | Ile | Val | Pro | Ser | Ala | Met | Ser |
|   |   |   |   | 395 |   |   |   | 400 |   |   |   | 405 |
| Leu | Ser | His | Gly | Leu | Pro | Pro | Val | Ala | His | Pro | Pro | His | Ala | Pro |
|   |   |   |   | 410 |   |   |   | 415 |   |   |   | 420 |
| Ser | Pro | Gly | Gln | Thr | Val | Lys | Pro | Glu | Ala | Asp | Arg | Asp | His | Ala |
|   |   |   |   | 425 |   |   |   | 430 |   |   |   | 435 |
| Ser | Asp | Gln | Leu |   |   |   |   |   |   |   |   |   |

48 KD CELLULAR PHOSPHOPROTEIN CTBP

This invention was made with the U.S. Government support awarded by National Institute of Health. The U.S. Government may have certain rights in the invention.

BACKGROUND OF THE INVENTION

The E1a region of adenovirus 2 and 5 encodes two major proteins of 289 and 243 amino acids (289R and 243R). Both proteins contain two exons and are identical except for the presence of an internal 46 amino acid region unique to the 289R protein. While the 289R protein is required for productive viral infection, the 243R protein encodes all the functions necessary for immortalization of primary cells and for transformation of these cells in cooperation with other viral or cellular oncogenes (2). Exon 1 of the E1A proteins is essential for these transforming activities and controls cell proliferation and transformation by modulating gene expression through interaction with several cellular proteins. One of the functional domains of exon 1 encompasses two regions, conserved (CR) region CR1 and CR2, that are conserved among different adenovirus strains. These regions are responsible for interactions between E1A and the cellular proteins pRb, p107 and p130, which cause these cellular proteins to release the E2F transcription factor, thus activating gene expression (reviewed by Dyson and Harlow, [3]; Nevins, [4]; Moran, [5]; Bayley and Mymrik, [6]). A second functional domain, encompassing the CR1 and the N-terminus of E1A, interacts with a transcriptional adapter p300 (5, 7, 8, 9) implicated in transcriptional repression of certain genes. Thus, the transforming activities of exon 1 appear to be linked to interactions with cellular proteins and the resulting regulation of transcription.

Although the functions of exon 2 have been studied less intensively, it has been implicated in certain positive and negative transcriptional regulatory activities (10, 11, 12). Exon 2 is required for immortalization (13, 14) and induction of Ad2/5-specific cytotoxic lymphocytes (15). In addition, exon 2 influences the extent of oncogenic transformation. Deletions within the C-terminal 67 amino acids of the E1A 243R protein enhance E1A/T24 ras cooperative transformation (13, 16), and tumorigenesis of transformed cells in syngeneic and athymic rodent models (13). Importantly, exon 2 also plays a role in tumor metastasis. Expression of wt E1A efficiently suppresses the metastatic potential of tumor cells (17, 18, 19). In contrast, cells expressing E1A proteins lacking the C-terminal 67 amino acids are highly metastatic (10, 13). Thus, exon 2 appears to negatively modulate in vitro transformation, tumorigenesis and metastasis. The activities of exon 2 have been localized within a 14 amino acid region (residues 225 to 238) near the C-terminus of the 243R protein (1). These transformation restraining activities of the C-terminal region of E1A correlate with the interaction of a 48 kD cellular phosphoprotein termed CtBP (1).

SUMMARY OF THE INVENTION

An object of the instant invention is to provide a protein, and the nucleotide sequence that encodes the protein, which interacts with Adenovirus E1A protein.

Another object of the invention is to provide and establish the identity of the protein which interacts with Adenovirus E1A protein, said protein is a cellular 48 kD phosphoprotein, commonly termed as CtBP.

Yet another object of the present invention is to provide amino acid sequence of Adenovirus E1A protein, and the nucleotide sequence that encodes the amino acid sequence, which interact with the 48 kD CtBP protein.

BRIEF DESCRIPTION OF THE DRAWINGS

The invention is further explained with reference to the following drawings

FIG. 3. Coimmunoprecipitation of 48 kD protein and E1A. The 48 kD protein (#30) and E1A proteins (243R or dl1135) were expressed in BSC40 cells using the recombinant vaccinia virus expression system. Proteins were immunoprecipitated with E1A specific antibody M58 or the antiserum raised against the 48 kD protein (anti#30) and analyzed on 10% SDS-PAGE.

FIG. 4. Phosphorylation of 48 kD protein. HeLa cells were transfected with the plasmid pRcCMV-T7-30 (to express T7 epitope tagged 48 kD protein) and labeled with $^{35}$S-methionine/cysteine or $^{32}$P-orthophosphate. Immunoprecipitations were carried out using the T7 antibody or control mAb antibody. As a marker, 48 kD protein was also purified on GST-Cter beads by affinity chromatography. Proteins were analyzed on 10% SDS-PAGE.

FIG. 5. Mapping of binding site for 48 kD protein. (A) Binding of E1A mutants to GST-48 kD (GST-30) protein. The $^{35}$S-labeled E1A proteins were incubated with GST or GST-48 kD (GST-30) protein. Bound proteins were eluted and analyzed on an 8% SDS-PAGE. 12H/235R refers to wt Ad12 E1A protein. This protein migrated in an anamolous fashion in SDS-PAGE. (B) The the C-terminal sequences of Ad2 243R and wt Ad12 235R proteins that were used in binding experiments. The conserved sequence motif is indicated with capital letters. 243R mutants (ΔPL, ΔDL, ΔSC) carry two amino acid substitutions within the conserved region. The 14 amino acid deletion of dl1135 (residues 225–238) includes the conserved motif and is shown on top.

FIG. 6. (A) Amino acid sequence of CtBP (SEQ.ID. No:1), derived from the nucleic acid sequence of cDNA listed in FIG. 7 (SEQ.ID. No:2). Underlined sequences correspond to peptide sequences A and B. (B) Sequence homology between CtBP and VanH. The alignment of CtBP and the *Enterococcus faecium* vancomicin resistence gene (VanH [32]) shows 67% similarity and 50% identity over the indicated regions. The boxed His residue corresponds to His$_{296}$ of D-LDH from *Lactobacillus plantarum*. This residue has been implicated in the catalytic activity of this dehydrogenase (47). Vertical lines indicate identical amino acids; : indicate similar amino acids.

FIG. 7. Nucleic acid sequence of cDNA (SEQ.ID. No:1) which encodes a protein which interacts with Adenovirus E1A protein.

BRIEF DESCRIPTION OF THE MATERIALS AND METHODS USED IN THE INVENTION

Plasmids. Plasmids encoding fusion proteins consisting of the Gal4 DNA-binding domain (1–147) and the entire second exon of the E1A 243R protein (aa 141–243) or a smaller C-terminal region (aa 176–243) were constructed in the yeast shuttle vectors pMA424 (20) or pAS1 (21). The exon 2 mutants dl181–193 (1), dl1133, 1134, 1135 and 1136 (9) were cloned into pMA424 in a similar fashion. Plasmids pGST-Cter, pGST-Cter (dl181–193) and pGSTdl1133–dl1136 have been described (1). Plasmids pTM1–30, pGEX–30 and pET21–30 were constructed by cloning the protein coding sequences (amplified by PCR) of the cDNA clone pAct30 in vectors pTM1 (22), pGEX-5X3 (Pharmacia) and pET21b (Novagen). Plasmid pCMV-T7-30 was constructed by cloning the T7-tagged cDNA from pET21b-30 in an expression vector pCMV (L. K. Venkatesh and G. C., unpublished). Plasmid pRcCMV-T7-30 was constructed by subcloning a fragment (SnaBI-HindIII) containing a portion of the CMV promoter and T7-tagged cDNA from pCMV-T7-30 into pRcCMV (Invitrogen). The 243R substitution mutants, ΔPL, ΔDL and ΔSC (see FIG. 5B) were constructed by PCR using primers designed to substitute Ala-Ser residues for the two amino acids targeted for mutation. The coding sequences of E1A 243R, dl1135 and the substitution mutants ΔPL, ΔDL and ΔSC were cloned into pTM1 (22). The coding sequence of Ad12 235R (12S) was subcloned into pcDNA3 (Invitrogen).

Two hybrid screening. The yeast two hybrid screen was carried out essentially as described by Chien et al., (23) and Durfee et al., (21). The yeast strain GGY1::171 (24) was cotransfected with pMA-Exon 2 and a human (B-cell) cDNA library tagged with the Gal4 activation domain (21). Positively interacting cDNA clones were further screened using a battery of ten different heterologous protein baits.

In vitro and in vivo protein interactions. In vitro protein interactions using $^{35}$S-labeled CtBP or E1A proteins with indicated GST fusion proteins were carried out as described by Boyd et al., (1). For immunoprecipitation analysis, CtBP and E1A proteins were expressed using the vaccinia virus/T7 RNA polymerase system described by Ausubel et al., (26). BSC40 cells were infected with vTF7-3 recombinant vaccinia virus that expresses T7 RNA polymerase (27) and then cotransfected with the plasmids pTM1-243R or pTM1-dl1135 and pTM1–30 using LipofectAMINE (GibcoBRL). Cells were labeled with $_{35}$S methionine/cysteine mixture (500 µCi/75 cm$^2$ flask) and subjected to immunoprecipitation (1).

Phosphorylation. HeLa cells were LipofectAMINE-transfected with the plasmid pRcCMV-T7-30 which expresses T7 epitope-tagged CtBP. Forty-eight hours after transfection, cells were labeled for 20 minutes with 4 mCi H$_3$$^{32}$Po$_4$ or with $^{35}$S methionine/cysteine, lysed and subjected to immunoprecipitation using the T7 mAb (Novagen) or control mAb (pAb416; Oncogene Science).

Purification and peptide sequence analysis of endogenous CtBP. Approximately 2.5×10$^{11}$ cells HeLa cells were lysed in E1A lysis buffer. The lysate was clarified by centrifugation and preincubated with 20 mg of GST immobilized on glutathione agarose, then incubated with 1 ml GST-Cter beads containing 5 mg of protein. The beads were washed 5X with E1A lysis buffer. The bound protein was separated by SDS-PAGE and blotted onto nitrocellulose. Bands stained with 1% amido black were excised from the membrane and after in situ tryptic digestion, peptides were separated by reverse phase HPLC, and sequenced in an ABI 477A protein sequencer (gas phase sequenator).

DETAILED DESCRIPTION OF THE INVENTION

A cDNA clone for a 48 kD phosphoprotein that specifically interacts with Adenovirus E1A protein and more specifically the C-terminal region (amino acids 229–238) of the adenovirus type 2/5 E1A 243R protein has been identified. This interaction was confirmed by in vitro protein binding and in vivo coimmunoprecipitation studies. Peptide sequences that were obtained from purified CtBP matched sequences in the predicted open reading frame of the cDNA clone. The peptide sequences were obtained from CtBP purified from HeLa cells, while the cDNA clone was isolated from a B-cell library. However, both proteins are indistinguishable with respect to their apparent molecular weight, binding properties and phosphorylation state. Furthermore, the polyclonal antibody raised against recombinant CtBP recognizes endogenous CtBP from HeLa cells. Taken together, these data indicate that the 48 kD protein encoded by the cDNA clone (#30) is CtBP.

CtBP binds within the same region (amino acid 225 to 238) of the E1A protein that modulates the in vitro transformation efficiency and tumorigenesis of E1A/T24 ras transformed BRK cells (1). E1A mutants that lack the C-terminal 67 amino acids or a 14 amino acid region (amino acid 225–238) encompassing the CtBP binding domain (amino acid 229–238) cooperate more efficiently with T24 ras in in vitro transformation assays than wt 243R. In addition, the mutant E1A/T24 ras transformed BRK cells form rapidly growing metastatic tumors in nude mice, and they even form tumors in syngeneic rats. It therefore appears that the second exon of E1A has a tumor suppressor activity and this function is linked to its ability to interact with CtBP.

Interestingly, CtBP displays significant homology to enzymes of the D-2-hydroxy acid dehydrogenase family (31, 32). Members of this family have so far only been identified from bacteria, plants and lower fungi (31–39). CtBP might encode an novel mammalian enzyme, whose activity somehow affects transformation and tumorigenesis. Tumor cells differ from their untransformed counterparts not only in quantitative changes of growth rate and cell division, but also in dramatic qualitative changes of their energy metabolism (reviewed by L. G. Baggetto, [40]). Some of these changes are associated with the activity of specific isoenzymes (40). CtBP may be such an enzyme, whose activity is sensitive to E1A. However, it has not been possible to detect any dehydrogenase enzyme activity or NAD-binding activity for CtBP. It is possible that the homology between CtBP and the dehydrogenase family constitutes the preservation of structural rather than enzymatic features. Members of this particular family of dehydrogenases have been shown to form homodimers (35). CtBP may be able to enter enzyme complexes and thereby modulate their activity. This complex could then be stabilized or disrupted by E1A.

Although the various dehydrogenases are considered to be enzymes primarily involved in energy metabolism, a number of surprising activities have been associated with various proteins within this family. For example, the nuclear uracil glycosylase activity that is deficient in Bloom's syndrome is associated with glyceraldehyde-3-phosphate dehydrogenase (41). Similarly, a nucleic acid helix-destabilizing activity is associated with lactate dehydrogenase-5 (42). More recently certain dehydrogenases have been implicated in mRNA transport (43, 44, 45). In addition, protein kinase activities have also been associated with certain dehydrogenases (42). Thus, it is possible that CtBP may also exhibit novel activities. It is intriguing to note that a DNA binding activity is associated with the C-terminal region of Ad2 E1A (46) that is significantly enhanced by a cellular cofactor. It could be speculated that CtBP may be a candidate for such a cofactor.

So far, CtBP is the only protein identified that binds to the second exon of E1A. The extensive genetic and biochemical analysis of exon 1 binding proteins has helped to understand key regulatory events in cell cycle control and oncogenic transformation. Such biochemical analysis of CtBP may help to understand the regulatory functions of exon 2 on tumorigenesis and metastasis.

The invention now will be described by reference to the following examples.

EXAMPLE 1

Figure 1:
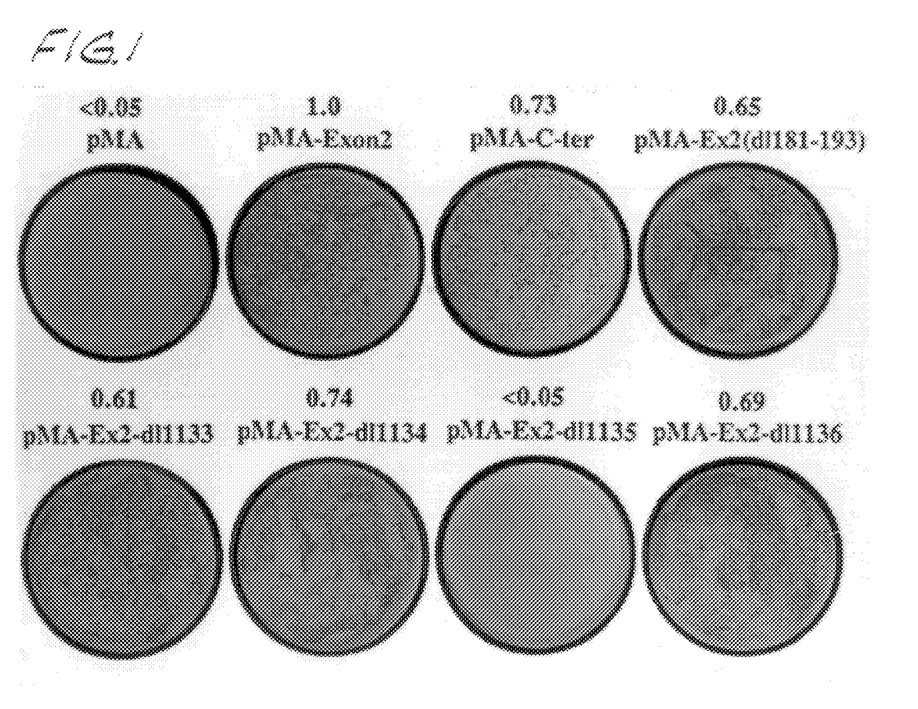
FIG. 1. Interaction of clone pAct30 with different E1A exon 2 mutants in yeast. The yeast strain GGY1::171 was transformed with pAct30 and a second plasmid coding for the Gal4 DNA-binding domain fused to various E1A exon 2 mutants as indicated in (A). Transformants were analyzed by X-gal filter assay for β-galactosidase expression (B). The relative levels of β-galactosidase expression obtained from quantitative ONPG colorimetric assays are given on top (B).

Cloning of cDNA for exon 2 binding protein: Yeast two hybrid system (23, 29) was used to identify cDNAs for cellular proteins that interact with exon 2 of Ad2 E1A. The two hybrid screen was carried out using yeast strain GGY1::171 (20) which contains the lacZ reporter gene under the control of the GAL1 promoter (24). GGY1::171 cells were transformed with a bait plasmid (pMA-exon 2) expressing Ad2 exon 2 (residues 141 to 243 of 243R) fused to the DNA binding domain of Gal4 (residues 1–147) in plasmid pMA424 (20) and a Gal4 activation domain tagged B-cell cDNA library (21). Approximately $10^7$ transformants were screened and a single clone (pAct30) that was strongly positive for interaction with the exon 2 bait was isolated. pAct30 specifically interacted only with the exon 2 bait and not with any of ten other heterologous baits (not shown). The interaction was further confirmed using a different indicator strain, Y153 (21). To identify the region within exon 2 which is required for interaction with the protein encoded by pAct30, two hybrid interaction studies were performed using plasmids expressing the Gal4 (1–147)-exon 2 fusion proteins containing various E1a mutants (1, 12). The interactions were analyzed both qualitatively and quantitatively (FIG. 1). The protein encoded by pAct30 interacted positively with all exon 2 mutants except dl1135 (residues 225 to 238; see FIG. 5B). As previously reported dl1135 is also defective in interaction with CtBP (1). Thus, the protein coded by pAct30 interacts with the E1A 243R protein within the same region (residues 225–238) required for CtBP interaction.

EXAMPLE 2

Figure 2A:
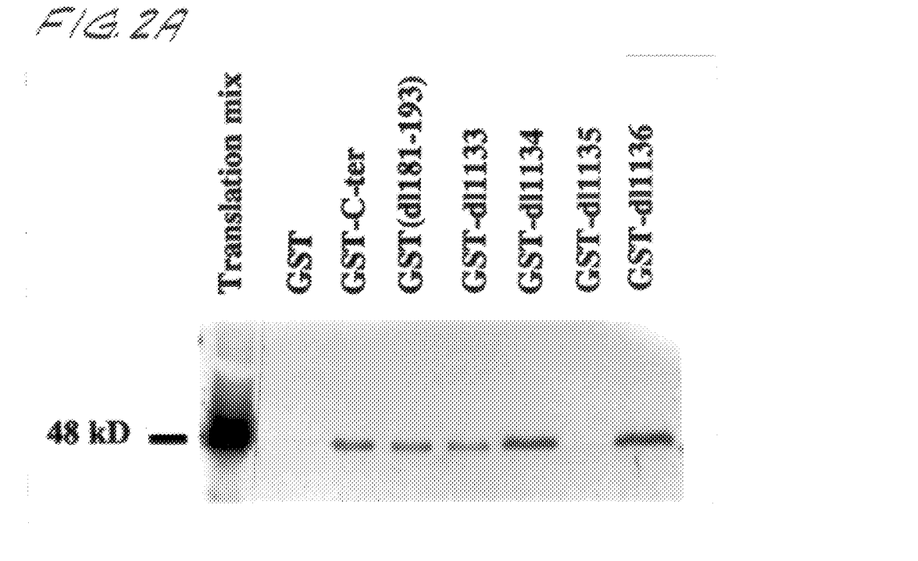
FIG. 2. In vitro interaction of 48 kD protein with E1A 243R mutants. (A) Binding of 48 kD protein to GST-Cter and various GST-Cter mutants of E1A (see FIG. 1A). (B) Binding of full length E1A (243R and dl1135) to GST-48 kD (GST-30). Proteins eluted from GST beads were analyzed on 10% SDS-PAGE.
Figure 2B:
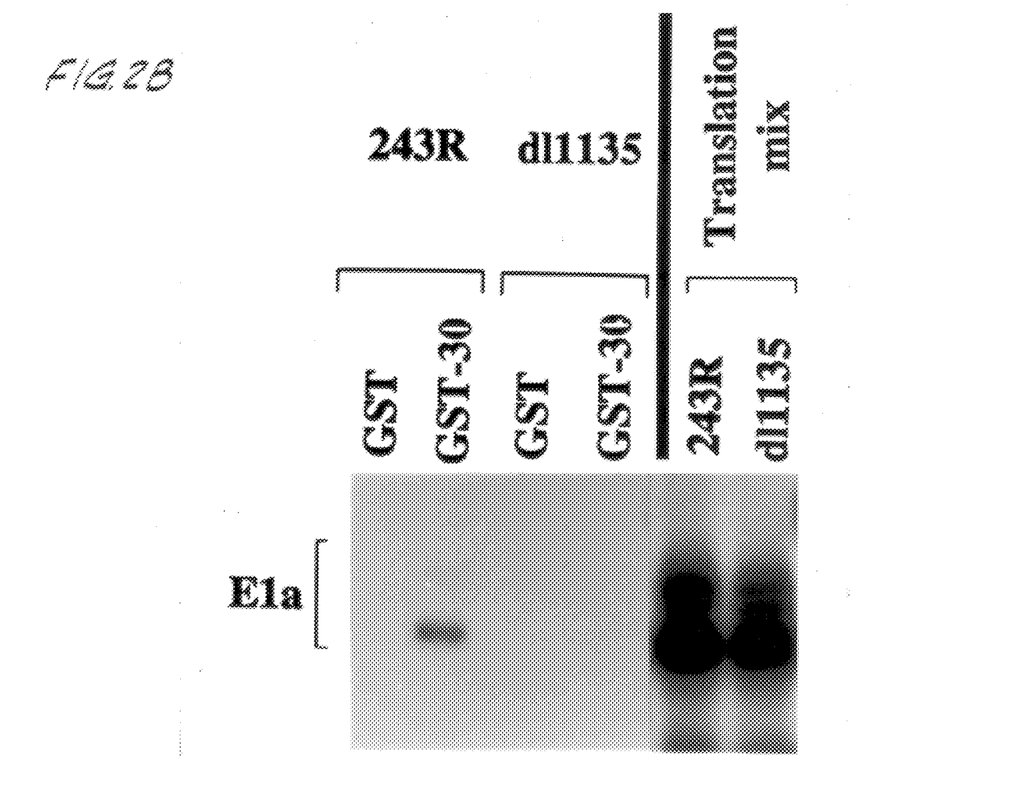

In vitro and in vivo Drotein interactions: To confirm the results obtained in the two-hybrid interaction studies, a series of in vitro and in vivo protein interaction studies were carried out. The coding sequence of pAct30 (lacking the Gal4 activation domain) was subcloned in a plasmid vector, pET21b under the transcriptional control of the bacteriophage T7 promoter. In vitro transcription and translation from the pET21b plasmid containing pAct30 sequences (pET21b-30) produced a 48 kD protein (hereafter designated as 48 kD). The interaction between this 48 kD protein and exon 2 was first analyzed by an in vitro protein binding assay using E1A-GST fusion proteins containing the C-terminal 68 amino acids of E1A (GST-Cter; 1). $^{35}$S-labeled 48 kD protein was assayed for binding to various GST-Cter mutant fusion proteins immobilized on GST affinity matrix followed by SDS-PAGE (FIG. 2A). The 48 kD protein did not bind significantly to either GST or GST-dl1135 protein but did interact with GST-Cter wt and various other GST-Cter mutant proteins. In a converse experiment, binding of $^{35}$S-labeled full length 243R wt or dl1135 protein to a GST-48 kD (GST-30) fusion protein was also carried out (FIG. 2B). As expected, the wt 243R protein did bind to the GST-48 kD protein while there was no detectable binding of the dl1135 protein. These in vitro binding studies indicate that the 48 kD protein coded by clone 30 interacts with the C-terminus or full length 243R protein and not with an E1A 243R mutant protein (dl1135) lacking the previously characterized CtBP-interacting domain (residues 229 to 238 [1]).

Figure 3:
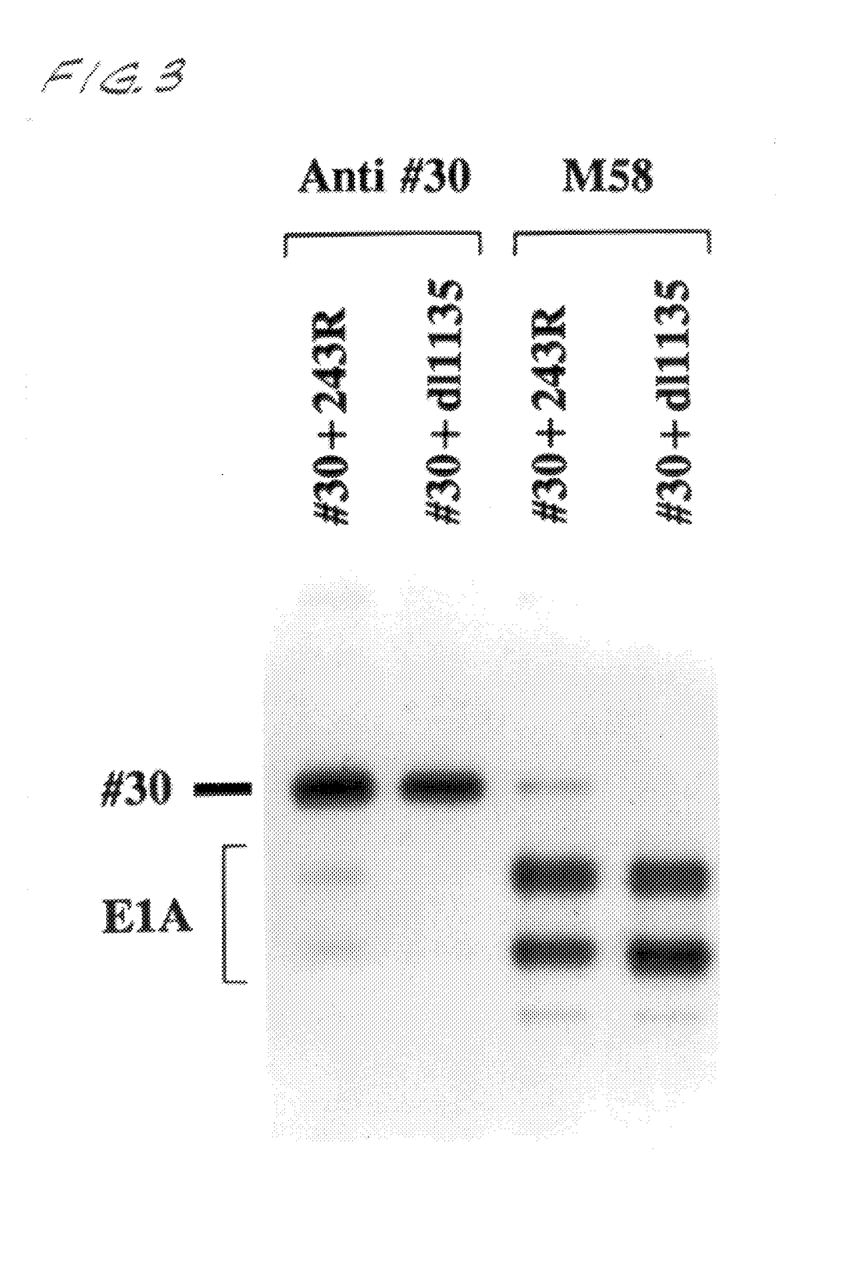

The interaction between the 48 kD protein and E1A 243R protein was also examined in an in vivo coimmunoprecipitation study. The 48 kD protein (#30) was co-expressed with the 243R wt or dl1135 protein in BSC40 cells using the vaccinia virus/T7 expression system (22). Cells were in vivo labeled with $^{35}$S-methionine/cysteine mixture, and cell lysates were subjected to immunoprecipitation with rabbit polyclonal antiserum prepared against the GST-48 kD fusion protein (anti #30) or an E1A monoclonal antibody, M58 (28). The wt 243R protein coprecipitated with the 48 kD protein, while the mutant dl1135 protein did not (FIG. 3). Conversely, the M58 (E1A) antibody coimmunoprecipitated the 48 kD protein from extracts containing 48 kD and 243R wt proteins and not from cells containing the 48 kD and dl1135 proteins. These results are in very good agreement with the in vitro binding studies and indicate that the 48 kD protein encoded by cDNA clone 30 interacts specifically within a region encompassing residues 225 to 238 in the manner previously reported for CtBP.

EXAMPLE 3

Figure 4:
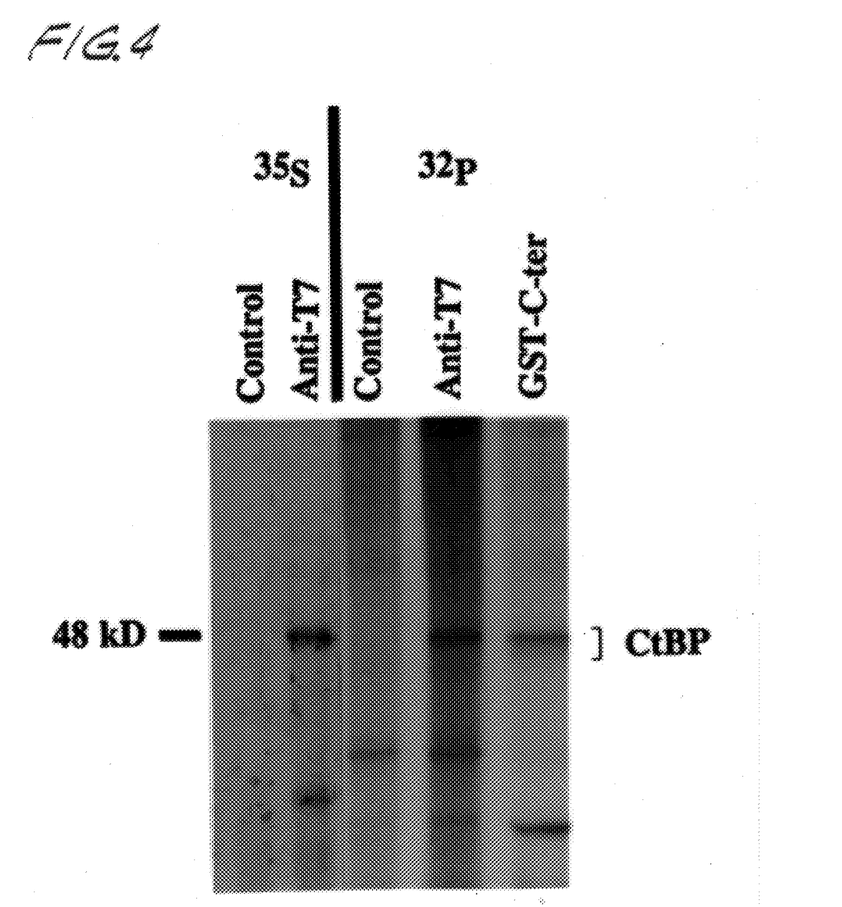

Phosphorylation of 48 kD protein: The 48 kD protein was tested to determine if it, like CtBP, is phosphorylated in vivo. HeLa cells were transfected with the plasmid pRcCMV-T7-30 which expresses the 48 kD protein tagged (at the N-terminus) with an 11 amino acid T7 epitope under the control of the CMV promoter. Cells were then labeled with $^{35}$S-methionine/cysteine or $^{32}$P-orthophosphate. The protein extracts were immunoprecipitated with a monoclonal antibody directed against the T7 tag. The $^{32}$P-labeled 48 kD protein was precipitated (FIG. 4), indicating that the 48 kD protein coded by clone 30 is a phosphoprotein like CtBP.

EXAMPLE 4

Figure 5A:
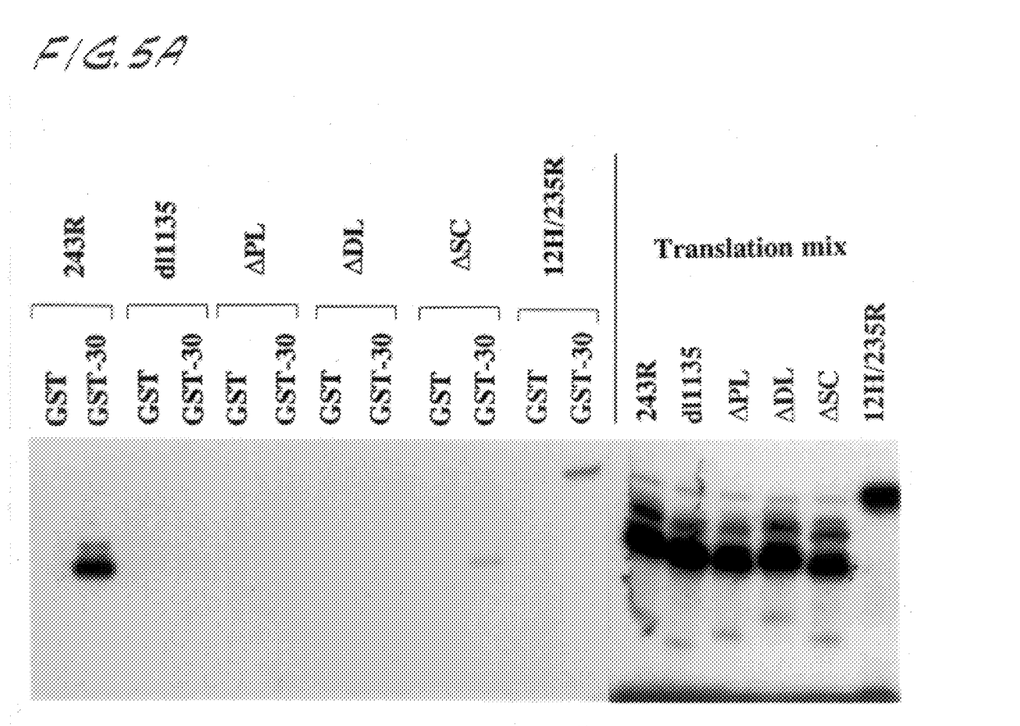
Figure 5B:
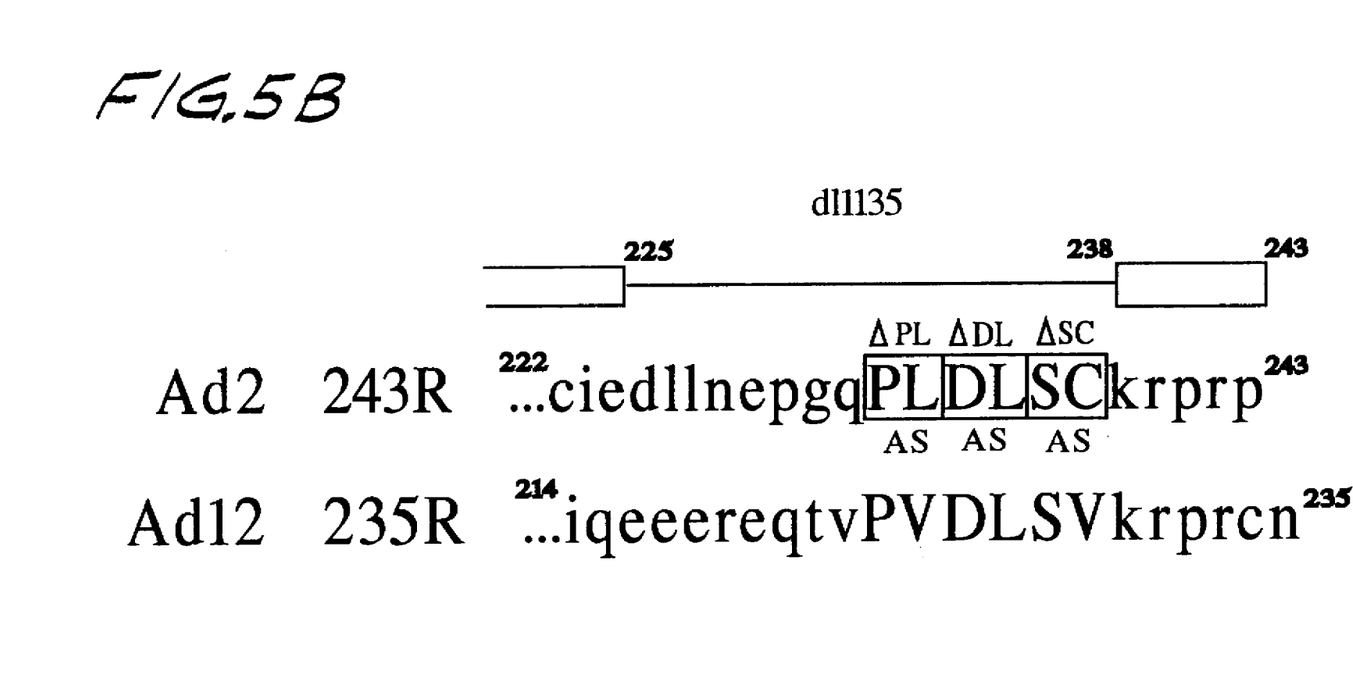

Binding site for the 48 kD protein: The CtBP binding domain of E1A is located in a nine amino acid region between residues 229 and 238 (1). Comparative analysis revealed that a six amino acid motif (PLDLSC; 233–238) is relatively well-conserved among adenovirus serotypes (30). To determine if these conserved amino acid residues constitute the binding site for the 48 kD protein, three two-amino acid substitution mutants (ΔPL, PL→AS; ΔDL, DL→AS; ΔSC, SC→AS; see FIG. 5B) were constructed and analyzed for in vitro binding activities. $^{35}$S-labeled mutant E1A proteins were prepared by coupled in vitro transcription and translation and tested for binding to GST-48 kD (GST-30) (FIG. 5A). No significant binding was observed for the substitution mutants ΔPL and ΔDL, comparable to the 14 amino acid deletion mutant dl1135. The mutant ΔSC did bind to the 48 kD protein, but at a very reduced level compared to 243R wt. It therefore appears that the six amino acid region analyzed (PLDLSC) is important for efficient binding of the 48 kD protein. The mutation ΔSC (SC→AS) results in the retention of a Ser residue albeit in a different position which may explain why this mutant still retains some in vitro binding activity. Alternatively, the PLDL region may constitute the core binding motif for the 48 kD protein with adjoining sequences playing an augmenting role. Ad12 E1A was tested which has a similar six amino acid motif near the C-terminus (PVDLSV versus PLDLSC; see FIG. 5B) for its ability to interact with the 48 kD protein. The in vitro binding experiments indicate that Ad 12 235R E1A (12H/235R) interacts with the 48 kD protein (GST-30), albeit at somewhat reduced level compared with Ad2 243R (FIG. 5A). These results suggest that the interaction of E1A with the 48 kD protein has been conserved during evolution.

EXAMPLE 5

Figure 6A:
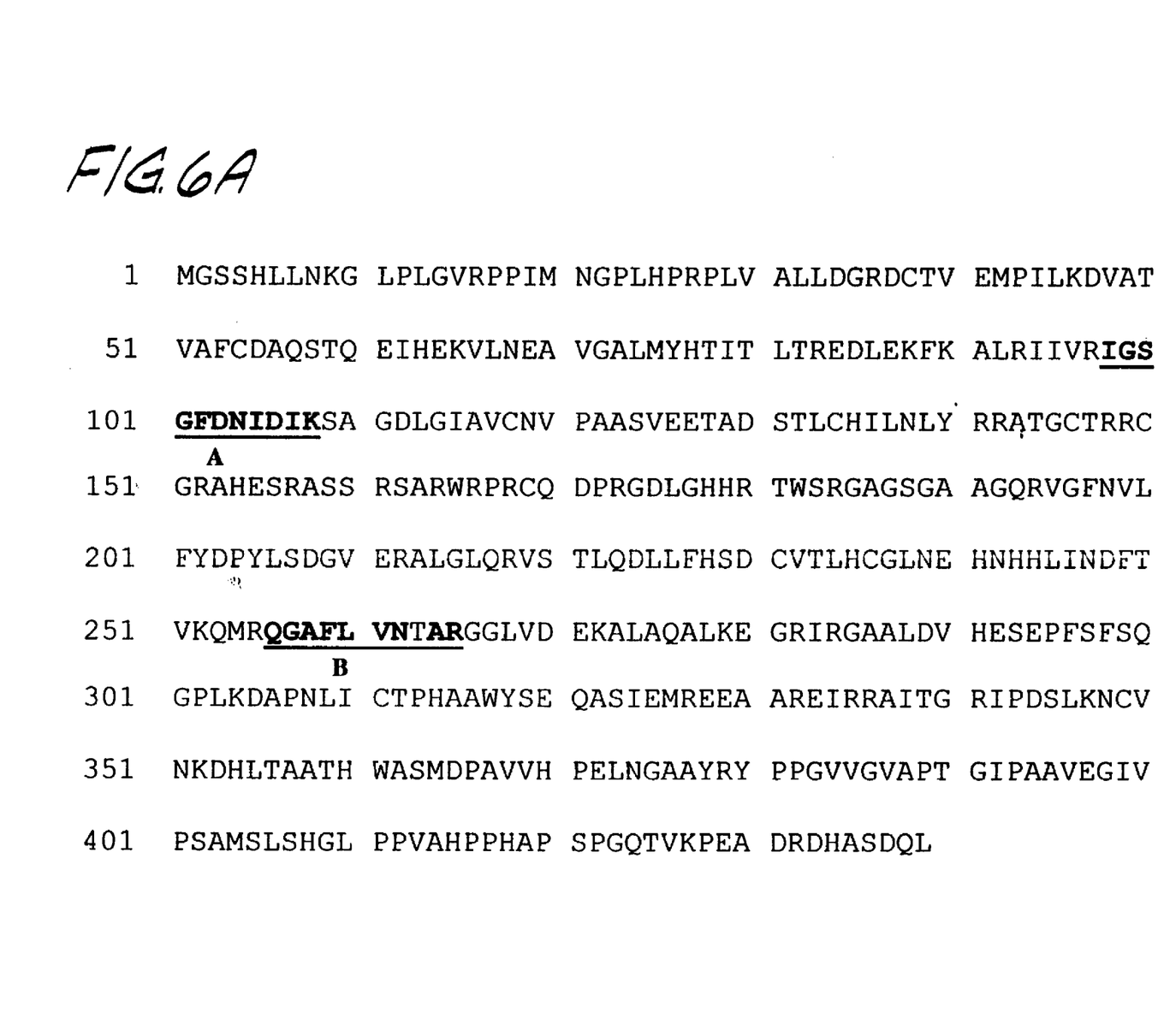

Sequence analysis of cDNA. The DNA sequence (SEQ.ID. No:1) (FIG. 7) of pAct30 was determined and the open reading frame (ORF) in relation to the Gal4 activation domain was established. These sequences revealed an ORF of 439 amino acids (predicted size: 47.5 kD) that starts from an ATG initiation codon located downstream of the Gal4 activation domain (SEQ.ID. No:2) (FIG. 6A). It was not possible to obtain additional protein-coding sequences by various methods. It therefore appears that pAct30 contains the entire protein coding sequences of the cDNA for CtBP.

In parallel studies, CtBP was purified from HeLa cell extracts using GST-Cter fusion protein immobilized on glutathione agarose affinity matrix. Purified CtBP was subjected to proteolysis and microsequencing. From these studies, amino acid sequences of two peptides were obtained: IGSGFDNIDIK (peptide A) and QGAFLVNAAR (peptide B). The predicted open reading frame of the cDNA clone (#30) contained sequences identical to peptide A (FIG. 6A).

There was a single amino acid variation between the sequences of peptide B and the corresponding sequence of the 48 kD open reading frame. The predicted sequence contains a Tyr residues at position 263 while the peptide B sequence contains an Ala at the corresponding position. It is possible that this variation may be due to an isoform of CtBP. The presence of the two peptide sequences in the 48 kD open reading frame further strengthens our conclusion that the cDNA clone #30 codes for CtBP.

EXAMPLE 6

Figure 6B:
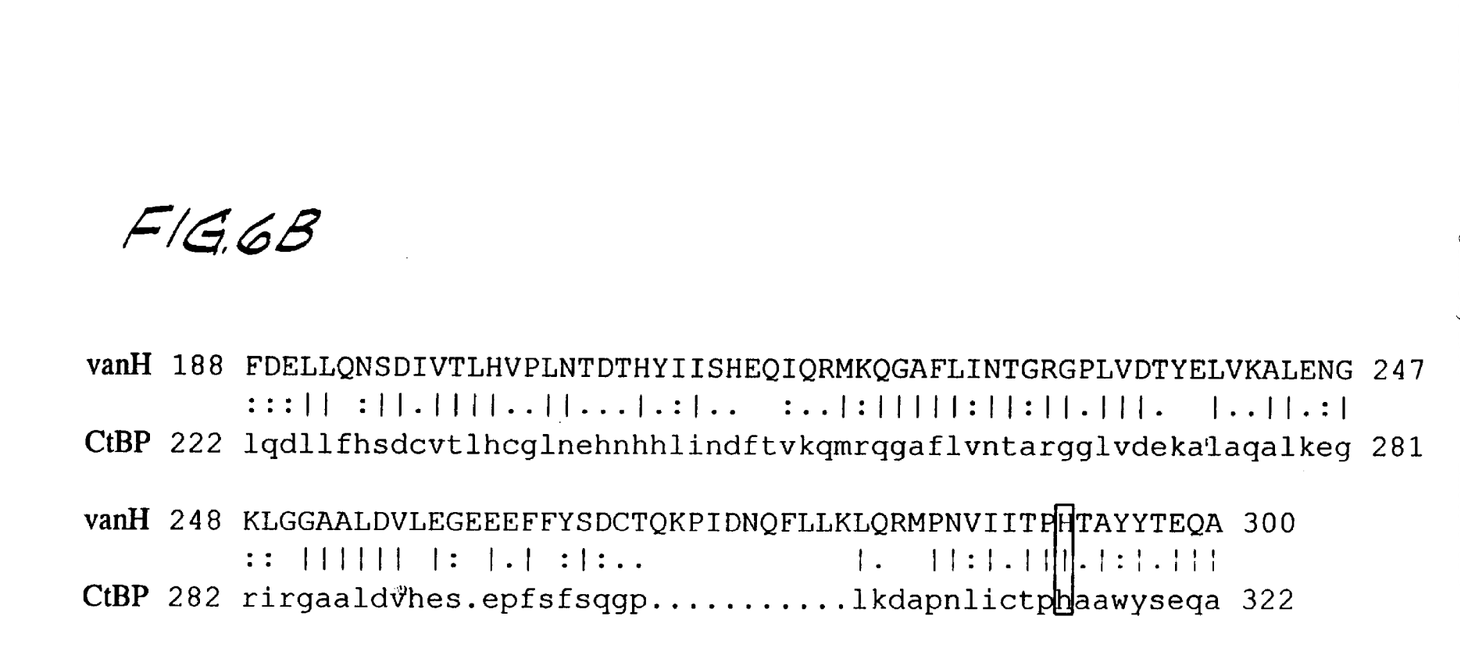

Homology of CtBP. Comparison of the amino acid sequences with known protein sequences revealed that CtBP shares significant homology with various NAD-dependent D-isomer specific 2-hydroxy acid dehydrogenases (31). The sequence alignment of CtBP and one of the 2-hydroxy acid dehydrogenases (32) is shown in FIG. 6B. However, it has not been possible to demonstrate any significant $NAD^+$-binding or dehydrogenase activity associated with CtBP using highly purified protein preparations or in cells infected with recombinant vaccinia virus expressing high levels of CtBP (not shown). Thus, it appears that despite the sequence similarity between CtBP and various dehydrogenases, CtBP may not possess a $NAD^+$-dependent dehydrogenase activity.

REFERENCES

1. Boyd, J. M., Subramanian, T., Schaeper, U., La Regina, M., Bayley, S. T. & Chinnadurai, G. (1993) *EMBO J.* 12, 469–478.
2. Zerler, B., Moran, B., Maruyama, K., Moomaw, J., Grodzicker, T. & Ruley, H. E. (1986) *Mol. Cell. Biol.* 6, 887–899.
3. Dyson, N. & Harlow, E. (1992) *Cancer Surveys* 12, 161–195.
4. Nevins, J. R. (1992) *Science* 258, 424–429.
5. Moran, E. (1993) *Curr. Op. Gen. Dev.* 3, 63–70.
6. Mymryk, J. S. & Bayley, S. T. (1994) *Int. J. Onc.* 4, 2131–2141.
7. Eckner, R., Ewen, M. E., Newsome, D., Gerdes, M., DeCaprio, J. A., Lawrence, J. B. & Livingston, D. M. (1993) *Genes Dev.* 8, 867–884.
8. Arany, Z., Newsome, D., Oldread, E., Livingston, D. M. & Eckner, R. (1995) *Nature* (London) 374, 81–84.
9. Lundblad, J. R., Kwok, R. P. S., Laurance, M. E., Harter, M. L. & Goodman, R. H. (1995) *Nature* (London) 374, 85–88.
10. Linder, S., Popowicz, P., Svensson, C., Marshall, H., Bondesson, M. & Akusjarvi, G. (1992) *Oncogene* 7, 439–443.
11. Bondesson, M., Svensson, C., Linder, S. & Akusjarvi, G. (1992) *EMBO J.* 11, 3347–3354.
12. Mymryk, J. S. & Bayley, S. T. (1993) *J. Virol.* 67, 6922–6928.
13. Subramanian, T., LaRegina, M. & Chinnadurai, G. (1989) *Oncogene* 4, 415–520.
14. Quinlan, M. P. & Douglas, J. L. (1992) *J. Virol.* 66, 2020–2030.
15. Urbanelli, D., Sawada, Y., Raskova, J., Jones, N. C., Shenk, T. & Raska, K. (1989) *Virology* 173, 607–614.
16. Douglas, J. L., Gopalakrishnan, S. & Quinlan, M. P. (1991) *Oncogene* 6, 2093–2103.
17. Pozzatti, R., Muschel, R., Williams, J., Padmanabhan, R., Howard, B., Liotta, L. & Khoury, G. (1986) *Science* 232, 223–227.
18. Pozzatti, R., McCormick, M., Thompson. M. A. & Khoury, G. (1988) *Mol. Cell. Biol.* 8, 2984–2988.
19. Steeg, P. S., Bevilacqua, G., Pozzatti, R., Liotta, L. A. & Sobel, M. E. (1988) *Cancer Res.* 48, 6550–6554.
20. Ma, J. & Ptashne, M. (1987) *Cell* 51, 113–119.
21. Durfee, T., Becherer, K., Chen, P. L., Yeh, S. H., Yang, Y., Kilburn, A. E., Lee, W. H. & Elledge, S. J. (1993) *Genes Dev.* 7, 555–569.
22. Moss, B., Elroy-Stein, O., Mizukami, T., Alexander, W. A. & Fuerst, T. R. (1990) *Nature* (London) 348, 91–92.
23. Chien, C. T., Bartel, P. L., Sternglanz, R. & Fields, S. (1991) *Proc. Natl. Acad. Sci. USA* 88, 9578–9582.
24. Gill, G. & Ptashne, M. (1987) *Cell* 51, 121–126.
25. Harlow, E., Whyte, P., Franza, B. R. Jr. & Schley, C. (1986) *Mol. Cell. Biol.* 6, 1579–1589.
26. Ausubel, F. M., Brent, R., Kingston, R., Moore, D., Seidman, J., Smith, J., & Struhl, K. (1992). *Current Protocols in Molecular Biology* (John Wiley & Sons, New York).
27. Fuerst, T. R., Niles, E. G., Studier, F. W. & and Moss, B. (1986) *Proc. Natl. Acad. Sci. USA* 83, 8122–8126.
28. Harlow, E., Franza, B. R. Jr. & Schley, C. (1985) *J. Virol.* 55, 533–546.
29. Fields, S. & Song, O. (1989) A novel genetic system to detect protein-protein interactions. *Nature* (London) 340, 245–246.
30. van Ormondt, H., Maat, J. & Dijkema, R. (1980) *Gene* 12, 63–76.
31. Taguchi, H. & Ohta, T. (1991) *J. Biol. Chem.* 266, 12588–12594.
32. Arthur, M., Molinas, C., Dutka-Malen, S. & Courvalin, P. (1991) *Gene* 103, 133–134.
33. Yomano, L. P., Scopes, R. K. & Ingram, L. O. (1993) *J. Bacteriol.* 175, 3926–3933.
34. Arps, P. J., Fulton, G. F., Minnich, E. C. & Lidstrom, M. E. (1993) *J. Bacteriol.* 175, 3776–3783.
35. Goldberg, J. D., Yoshida, T. & Brick, P. (1994) *J. Mol. Biol.* 236, 1123–1140.
36. Chistoserdova, L. V. & Lidstrom, M. E. (1994) *J. Bacteriol.* 176, 1957–1968.
37. Greenler, J., Sloan, J. S., Schwartz, B. W. & Becker, W. M. (1989) *Plant Mol. Biol.* 13, 139–150.
38. Colas de Francs-Small, C., Ambard-Bretteville, F., Small, I. D. & Remy, R. (1993) *Plant Physiol.* 102, 1171–1177.
39. Chow, C. M. & RajBhandary, U. L. (1993) *J. Bacteriol.* 175, 3703–3709.
40. Baggetto, L. G. (1992) *Biochimie* 74, 959–974.
41. Meyer-Siegler, K., Mauro, D. J., Seal, G., Wurzer, J., deRiel, J. K. & Sirover, M. A. (1991) *Proc. Natl. Acad. Sci. USA* 88, 8460–8464.
42. Williams, K. R., Reddigari, S. & Patel, G. L. (1985) *Proc. Natl. Acad. Sci. USA.* 82, 5260–5264.
43. Singh, R. & Green, M. R. (1993) *Science* 259, 365–368.
44. Elzinga, S. D., Bednarz, A. L., van Oosterum, K. Dekker, P. J. & Grivell, L. A. (1993) *Nucleic Acids Res.* 21, 5328–5331.

45. Kawamoto, R. M. & Caswell, A. H. (1986) *Biochemistry* 25, 657–661.
46. Ko, J. L., Dalie, B. L., Goldman, E. & Harter, M. L. (1986) *EMBO J.* 5, 1645–1651.
47. Taguchi, H. & Ohta, T. (1993) *J. Biol. Chem* 268, 18030–18034.

All references cited herein are incorporated herein by reference in entirety.

What I claim my invention is:

1. An isolated protein molecule consisting of SEQ ID NO:2.

2. An isolated nucleic acid molecule encoding the protein molecule of claim 1, whereby said nucleic acid molecule consisting of SEQ ID: 1.

* * * * *